(12) United States Patent
Miyazawa et al.

(10) Patent No.: US 6,608,103 B2
(45) Date of Patent: Aug. 19, 2003

(54) INHIBITOR FOR NEOVASCULATION, CELL MULTIPLICATION, LUMEN FORMATION AND FGF

(75) Inventors: Teruo Miyazawa, 17-7, Takamori 7-chome, Izumi-ku, Sendai-shi, Miyagi-ken, 981-3203 (JP); Heiji Ikushima, Toyama-ken (JP)

(73) Assignees: Fuji Chemical Industry Co., Ltd., Toyama (JP); Teruo Miyazawa, Sendai (JP)

( * ) Notice: Subject to any disclaimer, the term of this patent is extended or adjusted under 35 U.S.C. 154(b) by 0 days.

(21) Appl. No.: 10/061,539

(22) Filed: Feb. 1, 2002

(65) Prior Publication Data

US 2002/0183381 A1 Dec. 5, 2002

(30) Foreign Application Priority Data

Feb. 8, 2001 (JP) ......................................... 2001-032020

(51) Int. Cl.[7] ........................ A61K 31/355; A61K 31/35
(52) U.S. Cl. ........................ 514/458; 514/453; 514/455; 514/32
(58) Field of Search ................................. 514/458, 453, 514/455, 32

(56) References Cited

U.S. PATENT DOCUMENTS 6,251,400 B1 * 6/2001 Guthrie et al. .............. 424/439

FOREIGN PATENT DOCUMENTS

| EP | 0 742 012 | 11/1996 |
|----|-----------|---------|
| JP | 11049767 | 2/1999 |
| WO | WO 96/19214 | 6/1996 |
| WO | WO 99/15167 | 4/1999 |
| WO | WO 00/57876 | 10/2000 |
| WO | WO 00/78296 | 12/2000 |

OTHER PUBLICATIONS

Antiproliferative and Apoptotic Effects of Tocopherols and Tocotrienols on Preneoplastic and Neoplastic Mouse Mammary Epithelial Cells, by Barry McIntyre et al, Proceedings of the Society for Experimental Biology and Medicine (2000), vol. 224: 292–301.

Antitumor and Antioxidant Activity of Tocotrienols, by K. Komiyama et al, Lipid–Soluble Antioxidants: Biochemistry and Clinical Applications, 1992, 152–159.

Tocotrienols inhibit growth of ZR–75–1 breast cancer cells, by Kalanithi Nesarethnam et al, International Journal of Food Sciences and Nutrition (2000), 51 S95–S103.

Vitamin E Inhibits Experimental Carcinogenesis and Tumour Angiogenesis, by G. Shklar et al, Oral Oncol. Eur. J. Cancer., vol. 32B, No. 2, 1996, pp. 114–119.

Dietary and Nutritional Modulation of Tumor Angiogenesis, by Purna Mukherjee et al, Antiangiogenic Agents in Cancer Therapy, 1999, pp. 237–261.

The Merck Manual of Diagnosis and Therapy, by M.H. Beers, et al, p. 731.

* cited by examiner

*Primary Examiner*—William R. A. Jarvis
*Assistant Examiner*—Donna Jagoe
(74) *Attorney, Agent, or Firm*—Flynn, Thiel, Boutell & Tanis, P.C.

(57) ABSTRACT

This invention relates to an inhibitor having inhibitory activity against neovasculation, cell multiplication, lumen formation and fibroblast growth factor which comprises β-, γ- or δ-tocotrienol.

12 Claims, 1 Drawing Sheet

INHIBITOR FOR NEOVASCULATION, CELL MULTIPLICATION, LUMEN FORMATION AND FGF

BACKGROUND OF THE INVENTION

This invention relates to an inhibitor for neovasculation, cell multiplication, lumen formation and fibroblast growth factor (FGF), wherein the active component is a tocotrienol, and a food and a food additive containing tocotrienol.

Neovasculation is the formation of a new blood vessel from an existing blood vessel, and is composed of the following steps. (1) Neovasculation factor transfers a neovasculation signal to an endothelial cell, and the endothelial cell digests basement lamina and extracellular substrate in the neighborhood. (2) The hemoendothelial cell wanders while it multiplies. (3) The hemoendothelial cell forms lumen (neovasculation), and forms capillaries reticularly. It is observed that the neovasculation occurs on the onset and progress of diseases, such as a solid tumor, diabetic retinopathy, rheumatoid arthritis, hemangioma, periodontal disease, scleroderma, glaucoma, psoriasis and age-related macular degeneration, and it is considered to advance the progress of each disease. Various neovasculation inhibitors have been developed, but none of them have been put to practical use. Accordingly, it is still desired to develop a compound having safe neovasculation-inhibitory activity without side effects.

By the way, an inhibitor for the synthesis of heat-shock proteins having a molecular weight of 47 kilo daltons is known comprising tocopherol or a derivative thereof as an active component (JA09 040556A). The derivative includes the homologs of tocotrienol, i.e. $\alpha$-, $\beta$-, $\gamma$- and $\delta$-tocotrienols. The invention intends the treatment of diseases which produce extracellular matrices, such as cirrhosis of the liver and scleroderma, and discloses that the fibrosis accompanied with these diseases is caused by the increase of collagen synthesis, and that collagen synthesis increases with increasing the development of the above heat-shock proteins. Furthermore, it is pointed out that collagen synthesis in basement lamina exhibits an important role in neovasculation, and the inhibitor for the synthesis of heat-shock proteins is effective for the diseases based on the abnormal growth of neovasculation, i.e. diabetic retinopathy, glaucoma, rheumatic arthritis, etc. However, it is also taught that $\alpha$-tocopherol, which is vitamin E, is the most preferred, and only $\alpha$-tocopherol is shown in the Examples. Tocotrienols are only listed in the derivatives of tocopherol.

On the other hand, it is said that tocophenols have no action to inhibit neovasculation, the inventors also confirmed this matter in the following comparative examples.

SUMMARY OF THE INVENTION

An object of the invention is to provide an inhibitor exhibiting inhibitory action against neovasculation, cell multiplication, lumen formation and fibroblast growth factor (FGF), which has no problem in safety and is far superior to $\alpha$-tocopherol, and to contribute to the treatment of diseases caused by abnormal growth of neovasculation.

The inventors investigated eagerly in order to achieve the above object, and as a result, they found that tocotrienols, especially $\beta$-, $\gamma$-, $\delta$-tocotrienols, have a much greater inhibitory action against neovasculation, cell multiplication (cell growth), lumen formation and FGF than $\alpha$-tocopherol to complete the invention.

Thus, the present invention provides;

A neovasculation inhibitor which comprises $\beta$-, $\gamma$-, $\delta$-tocotrienol as an active component, A cell multiplication inhibitor which comprises $\beta$-, $\gamma$-, $\delta$-tocotrienol as an active component, A lumen formation inhibitor which comprises $\beta$-, $\gamma$-, $\delta$-tocotrienol as an active component, A fibroblast growth factor inhibitor which comprises $\beta$-, $\gamma$-, $\delta$-tocotrienol as an active component.=, A food containing a tocotrienol selected from the group consisting of $\alpha$-tocotrienol, $\beta$-tocotrienol, $\gamma$-tocotrienol and $\delta$-tocotrienol, and A food additive comprising a tocotrienol selected from the group consisting of $\alpha$-tocotrienol, $\beta$-tocotrienol, $\gamma$-tocotrienol and $\delta$-tocotrienol.

DETAILED DESCRIPTION OF THE INVENTION

Figure 1:
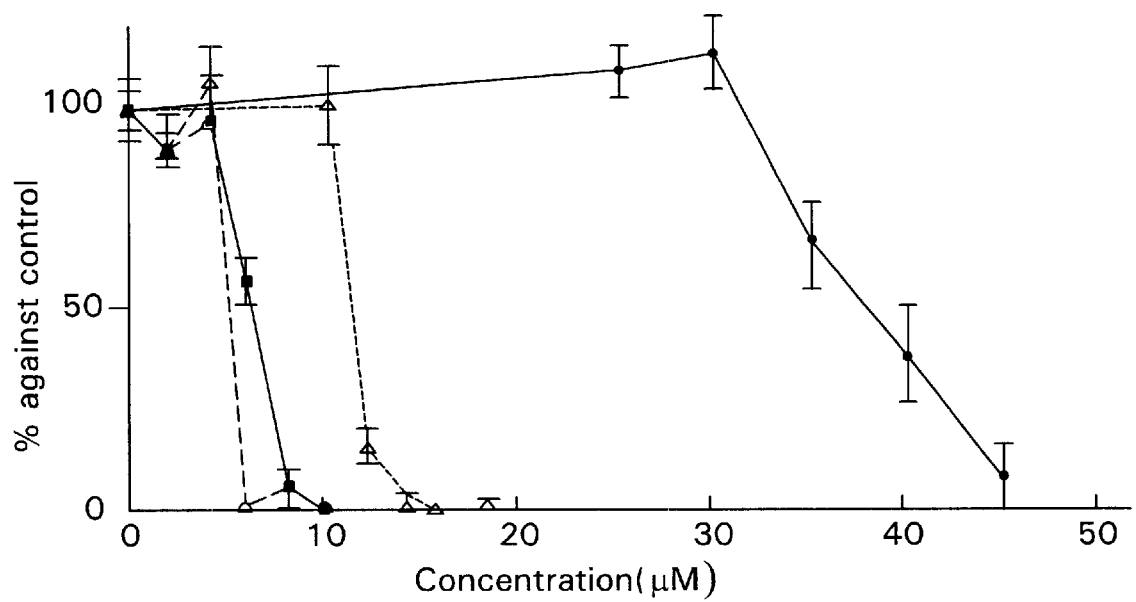
FIG. 1 is a graph showing the survival rate of cells with the concentration of tocotrienol. The numbers on the ordinate indicate relative survival rate of cell (% against control), and the numbers on the abscissa indicate concentration ($\mu$M) of tocotrienols which are DL-$\alpha$-tocotrienol (●), DL-$\beta$-tocotrienol (■), DL-$\gamma$-tocotrienol (Δ) and DL-$\delta$-tocotrienol (X).

There are four tocotrienol homologs for tocotrienol, which are $\alpha$-tocotrienol, $\beta$-tocotrienol, $\gamma$-tocotrienol and $\delta$-tocotrienol. Although all of them exhibit inhibitory action against neovasculation, cell multiplication, lumen formation and FGF, $\beta$-tocotrienol, $\gamma$-tocotrienol and $\delta$-tocotrienol exhibit a much greater inhibitory action than $\alpha$-tocotrienol. There are L-isomer, D-isomer and a racemic body for every tocotrienol, and they can be used for the invention. The tocotrienol applicable to the invention may be a mixture of two or more of $\alpha$-, $\beta$-, $\gamma$- and $\delta$-tocotrienols. In this case, it is enough that an effective amount of $\beta$-tocotrienol, $\gamma$-tocotrienol and/or $\delta$-tocotrienol exists in the mixture, $\alpha$-tocotrienol may be present or absent therein. Accordingly, when product extracted, separated from a raw material derived from a natural material contains $\alpha$-tocotrienol, it is not a problem because of not reducing effects of $\beta$-, $\gamma$- and $\delta$-tocotrienol by interaction with $\alpha$-tocotrienol. Rather, the content of $\alpha$-tocotrienol in the mixture is set in terms of medical effect, facilitation in taking and purification cost.

Each of the above tocotrienols may be in the form of an ester capable of releasing tocotrienol in vivo, and a preferable ester is with a saturated or unsaturated fatty acid.

The tocotrienol can be produced by pressing a natural material, extraction from a natural material, synthesis or the like. A general method is extraction from pericarp and/or seeds of a Palmae plant. Tocotrienol obtained from the extract of a natural material is a mixture of plural tocotrienol homologs.

The production of tocotrienol from a natural material can be conducted according to a known method. For example, water is added to the extract and a water layer is separated. The remaining oil layer is purified by column chromatography to obtain tocotrienol not containing or containing a trace amount of tocopherol. The rate and content of each tocotrienol homolog can be determined by a conventional method, such as liquid chromatography, particularly HPLC.

Each of $\alpha$-, $\beta$-, $\gamma$- and $\delta$-tocotrienols is commercially available, and also, each of them can be isolated from extracted and concentrated tocotrienol by a conventional method by further subjecting it to column chromatography.

Each inhibitor of the invention may be composed of tocotrienol alone or with other components according to the use or the like. Examples of the other components are water and palm oil. The content of water, palm oil or the like is not limited, and set according to the drug form or the like, and for example, 0.01 to 99 wt. %, particularly 0.01 to 90 wt. % for liquid drug.

Each inhibitor of the invention can be applied as a drug and preventative of diseases to which its inhibitory activity is exhibited. The subject diseases for the neovasculation inhibitor are solid tumors, diabetic retinopathy, retinal venoocclusive, retinopathy of prematurity, rheumatoid arthritis, hemangioma, periodontal disease, scleroderma, neovascular glaucoma, psoriasis, age-related macular degeneration, etc., and the subject diseases for cell multiplication inhibitor are solid tumors, diabetic retinopathy, rheumatoid arthritis, hemangioma, periodontal disease, scleroderma, glaucoma, psoriasis, age-related macular degeneration, etc. The subject diseases for lumen formation inhibitor are solid tumors, diabetic retinopathy, rheumatoid arthritis, hemangioma, periodontal disease, scleroderma, glaucoma, psoriasis, age-related macular degeneration, etc., and the subject diseases for FGF inhibitor are solid tumors, diabetic retinopathy, rheumatoid arthritis, hemangioma, periodontal disease, scleroderma, glaucoma, psoriasis, age-related macular degeneration, etc., since it inhibits growth of dermic cells, neovasculation and excess activation of cell multiplication by FGF. These diseases are not only of human but also of other animals, such as cattle, e.g. cow, horse, pig and sheep, poultries, e.g. chicken, quail and ostrich, pets, e.g. reptiles, birds and compact mammals, and fishes for cultivation.

Administration form is not limited, and the inhibitor can be prepared into various forms, such as tablets, sublingual tablets, pills, suppository, triturate, powder, parvules, granules, capsules, microcapsules, injection, emulsion, patches and the like. For example, tablets can be produced by mixing a pharmacologically acceptable carrier homogeneously with the composition, and then tableting the mixture. Triturate, powder and granules can be produced by rendering the composition into a solution or suspension together with a carrier, followed by drying by a conventional method, such as spray drying or lyophilizing.

On producing triturate, powder, parvules, granules, tablets or the like, it is possible to use various additives, such as an excipient, e.g. lactose, glucose, sucrose, and mannitol, disintegrator e.g. starch and sodium alginate, lubricant, e.g. magnesium stearate and talc, binder, e.g. polyvinyl alcohol, hydroxypropyl cellulose and gelatin, surfactant, e.g. fatty ester, plasticizer, e.g. glycerin, and so on.

To the pharmaceutical composition comprising the inhibitor of the invention, a further antioxidant may be added. The further antioxidant is not particularly limited, and may be any material having antioxidant action. Illustrative of the further antioxidants are vitamin A, such as retinol and 3,4-di-dehydroretinol, vitamin B, vitamin C, such as D-ascorbic acid and L-ascorbic acid, vitamin E, such as α-tocopherol, β-tocopherol, γ-tocopherol, δ-tocopherol, vitamin E acetate and vitamin E succinate, vitamin E phosphates, coenzyme Q, flavonoid, tannin, ellagic acid, polyphenols, radical inhibitor, hydroperoxide decomposer, metal chelating agent, active oxygen remover, carotenes, such as α-carotene, β-carotene, γ-carotene and δ-carotene, tocoquinone, and their pharmaceutically acceptable salts, and mixtures thereof.

Injections can be produced in a conventional manner where additive(s) may be added, such as pH adjustor, buffer, resolvent, suspending agent, isotonizing agent, stabilizer, antiseptic, etc. The injections may be lyophile preparations which can be produced in a conventional manner.

Illustrative of the suspending agents are polysorbate 80, methyl cellulose, hydroxyethyl cellulose, sodium carboxymethyl cellulose, polyoxyethylene sorbitan monolaurate, gum arabic, tragacanth powder, etc. Illustrative of the resolvents are polysorbate 80, hydrogenated polyoxyethylene castor oil, nicotinamide, polyoxyethylene sorbitan monolaurate, macrogol, castor oil fatty ethyl ester, etc. Illustrative of the stabilizers are sodium sulfite, sodium metasulfite, etc. Illustrative of the antiseptics are p-hydroxybenzoic acid methyl ester, p-hydroxybenzoic acid ethyl ester, sorbic acid, phenol, cresol, chlorocresol, etc.

A suitable content of β-, γ- or δ-tocotrienol (total content, in the case of two or more of them) in the pharmaceutical composition is 0.01 to 99 wt. %, preferably 1 to 99 wt. %. The dose of each inhibitor varies according to the type of disease, age, sexuality, body weight, and the degree of disease of the patient, administration form, and the like, and in general, about 30 to 3000 mg, preferably about 100 to 3000 mg/adult•day is administered orally or parenterally once or divided into two to four times.

The tocotrienols used in the invention are known to be safe compounds without recognizable chronic toxicity as well as acute toxicity (JA 58-096021A).

Upon applying the effective component of the invention to food, either of β-, γ- or δ-tocotrienol or a mixture thereof can be used. The tocotrienol can be used in a form of as it is, diluted with oil, emulsion or blended with a conventional carrier used in the food field.

The emulsion can be prepared by adding the tocotrienol or a mixture thereof to an oil phase portion, further adding a liquid oil, such as glycerin fatty acid ester, sorbitan fatty acid ester, sucrose fatty acid ester, glycerin, dextrin, rape seed oil, soybean oil or corn oil, and adding L-ascorbic acid or its ester or salt, gum, such as locust bean gum, gum arabic or gelatin, flavonoid or polyphenol, such as hesperidin, rutin, gelsemine, querucetin, catechin or a mixture thereof to a water phase portion, followed by emulsifying.

Drinks can be divided into alcoholic drinks and nonalcoholic drinks. Illustrative of alcoholic drinks are liqueurs and medical wines, and illustrative of nonalcoholic drinks are carbonated drinks, non-carbonated drinks, such as juice and nectar, refreshing drinks, such as juice and nectar, refreshing drinks, drinks for sports, tea, coffee or cocoa.

Illustrative of foods and drinks are cakes and candies, such as pudding, jelly, gumi candy, drops, caramel, chewing gum, chocolate, pastry buttery cream, custard cream, cream puff, pancake, bread, potato chips, fried potato, popcorn, biscuit, cracker, pie, sponge cake, waffle, cake, doughnut, cookie, rice cracker, millen and rice cake, bun with bean jam filling and candy, dry noodles, such as macaroni and pasta, egg products, such as mayonnaise and raw cream, drinks, functional drinks, lactic acid beverage, lactic acid bacterium drinks, concentrated milk drinks, fruit juice, drinks without fruit juice, nector, clear carbonated drinks, carbonated drinks with fruit juice, fruit-colored carbonated drinks, table luxuries, such as green tea, black tea, instant coffee, cocoa and coffee drink in a can, milk products, such as ice cream, yogurt, milk for coffee, butter, butter sauce, cheese, fermentation milk and processed milk, pastes, such as marmalade, jam, flower paste, peanut paste, fruit paste and fruit with syrup, stock meat products, such as ham, sausage, bacon, dry sausage, beef jerky and lard, fishery products, such as fish meat ham, fish meat sausage, boiled fish paste, fish cake, dried fish, dried bonito, sea urchin, salted guts of cuttle fish, dried cuttle fish, dried mirin-seasoned fish, dried shellfish and smoked salmon, etc., foods boiled down in soy, such as those of small fishes, shellfishes, edible wild plants, mushroom and sea tangle, curries, such as instant curry, retort curry and canned curry, seasonings, such as miso, miso powder, soy sauce, soy sauce powder, moromi, fish sauce, sauce, ketchup, oyster sauce, solid bouillon, seasoning for roast meat, curry roux, stew base, soup base, stock base, paste, instant soup, fish flour, dressing and salad oil, fried products, such as fried bean curd, cake of fried bead curd and instant chinese noodle, soybean milk, margarine and shortenings.

The above foods and drinks can be produced according to a conventional method by blending with raw materials therefor, followed by processing.

The blending amount of tocotrienol in the above foods and drinks varies depending on the form of food or drink, and in general, 0.001 to 10% is preferred. The blending amount is adjusted so as to take a necessary amount capable of inhibiting onset or progress of neovasculation. A suitable amount of the tocotrienol is 10 to 3000 mg, preferably 100 to 1000 mg/adult•day.

The above foods and drinks can be used as functional foods and drinks, nutrition supplements, or heath foods and drinks. Although the form is not especially limited, for example, the tocotrienol is blended into a protein having a high nutritional value with good amino acid balance, such as milk protein, soybean protein or egg albumin protein, their digestion products, oligopeptides of egg albumin, soybean digestion products, amino acid mixtures, etc. They can be in a form of soft capsules, tablets or the like.

The nutrition supplements and functional foods and drinks include liquid food, semi-digested nourishing meal, component nourishing meal, drinking agent, capsules, enteral nutrition. The above foods and drinks, for example, drinks for sports or nutrition can be blended with nutritional components, such as amino acids, vitamins and minerals, as well as, sweetener, spice, flavoring or coloring agent, in order to improve nutrition balance or flavoring.

It is also preferable to add an antioxidant, such as tocopherol, L-ascorbic acid, BHA or rosemary extract in order to stabilize tocotrienol.

The food and drinks of the invention can be for feed for cattle, poultry or pets, such as dry dog food, dry cat food, wet dog food, wet cat food, semi-moistened dog food, feed for chicken, and feed for stocks, such as cows and pigs. They can be prepared according to a conventional method.

EXAMPLES

Abbreviations in the examples are as follows;

MTT: 2-4,3-(4,5-dimethylthiazole-2-yl)-2,5-diphenyl tetrazolium bromide

LDH: Lactate dehydrogenase

MEM: Minimum essential medium

WST: 2-(4-iodophenyl)-3-(4-nitrophenyl)-5-(2,4-disulfophenyl)-2-H-tetrazolium monosodium salt Cells, culture conditions and samples (tocotrienols, $\alpha$-tocopherol and fibroblast growth factor (FGF)) used in the examples are as follows;

Cells:

Normal bovine aortic endothelial cells (BAEC) were manufactured by Cell Systems Co., and purchased through Dainippon Seiyaku Co., Ltd.

Culture Conditions:

A cell suspension was prepared by adding the cells to MEM (Sigma Chemical Co.) containing 10 v/v (%) fetal bovine serum (FBS), 20 IU/ml penicillin and 20 IU/ml streptomycin (MEM+10% FBS) in a concentration of $1\times10^5$ cells/ml, and cultured in a 5% $CO_2$ incubator at 37° C. by using a 60 mm dish coated with type I collagen with subculturing every 2 to 3 days.

Samples:

The tocotrienol mixture sample used consisted of 18.9 wt. % $\alpha$-tocotrienol, 22.6 wt. % $\gamma$-tocotrienol, 1.2 wt. % $\delta$-tocotrienol, 0.0 wt. % $\alpha$-tocopherol and 45.3 wt. % other (mainly water or palm oil).

As to tocotrienol homolog samples, commercial $\alpha$-tocotrienol, $\beta$-tocotrienol, $\gamma$-tocotrienol and $\delta$-tocotrienol (all DL-body, trade name "Tocotrienol", manufactured by (Calbiochem Co.) were dissolved in ethanol and subjected to testing.

The $\alpha$-tocopherol sample was prepared by dissolving a commercial $\alpha$-tocopherol (Wako Co.) in ethanol.

The fibroblast growth factor sample was prepared by dissolving a commercial FGF (Sigma Chemical Co.) in MEM (Sigma Chemical Co.)

Each of the above samples was added to MEM containing 2% (v/v) FBS, 20 IU/ml penicillin and 20 IU/ml streptomycin (MEM+2% FBS), and subjected to testing.

Examples 1–5

Effects of Tocotrienols on Multiplication of BAEC

Effects of tocotrienols on the multiplication of BAEC were examined by using MTT assay.

BAEC with confluent growth were treated with trypsin, and suspended in MEM+10% FBS in a concentration of $1\times10^4$ cells/ml. The cell suspension was placed in each well of four 96 well-microplates in an amount of 100 $\mu$l/well, and incubated overnight in a $CO_2$ incubator. The culture solution in each well was removed, and changed to 100 $\mu$l culture medium (MEM+2% FBS) containing a sample to continue incubation. Each one microplate was taken out after 0, 24, 48 or 96 hours from placing the culture medium containing a sample. In the case of the microplate taken out after 96 hours, the culture medium was once changed after 48 hours. 3 mg/ml MTT solution PBS (−) was put in each well in an amount of 50 $\mu$l/well, and incubated for 3 hours in a $CO_2$ incubator. After filling each well with phosphate buffered saline (PBS(−)), liquid in each well was evaporated, and isopropyl alcohol containing 0.04 mol/l HCL was put in each well in an amount of 200 $\mu$l/well. The microplates were allowed to stand overnight in a dark place, and then, absorbance at 595 nm and 655 nm (dual) was measured by a microplate reader.

The samples employed were the tocotrienol mixture, DL-$\alpha$-tocotrienol, DL-$\beta$-tocotrienol, DL-$\gamma$-tocotrienol and DL-$\delta$-tocotrienol. In the case of Control group A, no sample was added.

Comparative Example 1

The assay was carried out in the same manner as Example 1, except that α-tocopherol was substituted for DL-α-tocotrienol.

The results were summarized in Table 1, wherein the absorbance was mean value+SE(n=8).

TABLE 1

| | | Absorbance | | | |
|---|---|---|---|---|---|
| | Sample | 0 hr | 24 hrs | 48 hrs | 96 hrs |
| Cont. A | — | 0.091 ± 0.002 | 0.181 ± 0.004 | 0.316 ± 0.009 | 0.358 ± 0.010 |
| Ex. 1 | DL-α-Tocotrienol 10 μM | 0.090 ± 0.003 | 0.141 ± 0.008 | 0.271 ± 0.010 | 0.382 ± 0.014 |
| Ex. 2 | DL-β-Tocotrienol 10 μM | 0.084 ± 0.002 | 0.029 ± 0.004 | 0.39 ± 0.007 | 0.011 ± 0.002 |
| Ex. 3 | DL-γ-Tocotrienol 10 μM | 0.101 ± 0.002 | 0.020 ± 0.001 | 0.010 ± 0.002 | 0.003 ± 0.000 |
| Ex. 4 | DL-δ-Tocotrienol 10 μM | 0.103 ± 0.001 | 0.004 ± 0.000 | 0.003 ± 0.000 | 0.002 ± 0.000 |
| Ex. 5 | Tocotrienol Mix. 10 μM | 0.092 ± 0.002 | 0.130 ± 0.003 | 0.157 ± 0.007 | 0.249 ± 0.010 |
| Comp. 1 | α-Tocopherol 100 μM | 0.092 ± 0.003 | 0.140 ± 0.003 | 0.268 ± 0.004 | 0.520 ± 0.012 |

As can be seen from the results in Table 1, DL-β-tocotrienol, DL-γ-tocotrienol and DL-δ-tocotrienol exhibited remarkable inhibitory action against cell multiplication. On the other hand, the inhibitory action of DL-α-tocotrienol was similar to control group A, and α-tocopherol does not exhibit inhibitory action, nevertheless its concentration was 10 times as much as the tocotrienols.

Examples 6–11
Inhibitory Action of Tocotrienols against FGF

Inhibitory action of the tocotrienol mixture, DL-α-tocotrienol, DL-β-tocotrienol, DL-γ-tocotrienol and DL-δ-tocotrienol was examined against FGF activity by the MTT assay similar to Examples 1–5. In the case of Control group B, no sample was added.

Comparative Example 2

The assay was carried out in the same manner as Example 7, except that α-tocopherol was substituted for DL-α-tocotrienol.

The results were summarized in Table 2, wherein the absorbance was mean value±SE (n=8).

TABLE 2

| | | Absorbance | | | |
|---|---|---|---|---|---|
| | Sample | 0 hr | 24 hrs | 48 hrs | 96 hrs |
| Cont. B | — | 0.036 ± 0.002 | 0.059 ± 0.002 | 0.155 ± 0.005 | 0.215 ± 0.011 |
| Ex. 6 | FGF 20 ng/ml | 0.046 ± 0.001 | 0.092 ± 0.004 | 0.267 ± 0.004 | 0.251 ± 0.009 |
| Ex. 7 | FGF 20 ng/ml DL-α-Tocotrienol 10 μM | 0.044 ± 0.002 | 0.096 ± 0.004 | 0.290 ± 0.010 | 0.328 ± 0.018 |
| Ex. 8 | FGF 20 ng/ml DL-β-Tocotrienol 10 μM | 0.042 ± 0.002 | 0.036 ± 0.003 | 0.055 ± 0.005 | 0.039 ± 0.004 |
| Ex. 9 | FGF 20 ng/ml DL-γ-Tocotrienol 10 μM | 0.042 ± 0.002 | 0.085 ± 0.004 | 0.232 ± 0.016 | 0.431 ± 0.011 |
| Ex. 10 | FGF 20 ng/ml DL-δ-Tocotrienol 10 μM | 0.040 ± 0.002 | 0.003 ± 0.000 | 0.003 ± 0.000 | 0.003 ± 0.000 |
| Ex. 11 | FGF 20 ng/ml Tocotrienol Mix. 10 μM | 0.041 ± 0.002 | 0.077 ± 0.005 | 0.141 ± 0.010 | 0.108 ± 0.007 |

TABLE 2-continued

| Sample | | Absorbance | | | |
| --- | --- | --- | --- | --- | --- |
| | | 0 hr | 24 hrs | 48 hrs | 96 hrs |
| Comp. 2 | FGF 20 ng/ml α-Tocopherol 100 μM | 0.045 ± 0.002 | 0.080 ± 0.004 | 0.242 ± 0.014 | 0.360 ± 0.020 |

Examples 12–14
Neovasculation

BAEC was cultured between two layers of type I collagen gel, and a lumen-like netting structure formed therebetween was evaluated.

BAEC with confluent growth were treated with trypsin, and suspended in MEM+10% FBS in a concentration of $1 \times 10^5$ cells/1.5 ml. The cell suspension was placed in each well of a 12 well-microplate coated with type I collagen in an amount of 1.5 ml/well, and incubated overnight in a $CO_2$ incubator. Eight parts by volume of "Vitrogen Collagen" (Collagen Co.), 1 part by volume of 0.1 N NaOH and 1 part by volume of ×10 MEM (GIBCO BRL) were placed in a tube, and mixed quickly in an ice bath. The culture solution was removed by suction, and 0.5 ml/well of the above mixture containing collagen was pipetted into each well. The microplate was placed in a $CO_2$ incubator for about 30 minutes to gelatinize it. 1.5 ml of a medium (MEM | 2% FBS) containing a sample was added, and continued to incubate while changing the medium every second day.

The variation of cells were observed by a microscope by taking a photograph, and lumen formation was evaluated by counting the number of branches of cells forming lumen.

The results were summarized in Table 3, wherein the number of cells forming lumen was shown by mean value ±SE (n=4). In control group C, no sample was added.

TABLE 3

| Sample | | Conc. (μM) | Number of Cells Forming Lumen/cm² |
| --- | --- | --- | --- |
| Control C | — | — | 39.50 ± 1.85 |
| Example 12 | Tocotrienol Mixture | 25 | 0.00 ± 0.00 |
| Example 13 | Tocotrienol Mixture | 10 | 5.50 | 0.65 |
| Example 14 | Tocotrienol Mixture | 1 | 43.25 ± 1.49 |

From the above results, it can be seen that, by the presence of tocotrienol in a concentration of 2 μM or more, the number of cells forming lumen decreased, and in the case of 25 μM tocotrienol, cells forming lumen disappeared.

Examples 15–20
Inhibition against Lumen Formation

An inhibition test against lumen formation was carried out similar to Examples 12–14, wherein the tocotrienol mixture was replaced by DL-α-tocotrienol, DL-β-tocotrienol, DL-γ-tocotrienol and DL-δ-tocotrienol.

Comparative Example 3

The inhibition test against lumen formation was carried out in the same manner as Example 15, except that α-tocopherol was substituted for DL-α-tocotrienol.

The results are summarized in Table 4, wherein the number of cells forming lumen/cm² are shown by mean value ±SE (n=4).

In Control group D, no sample was added.

TABLE 4

| | Sample | Conc. (μM) | Number of Cells Forming Lumen/cm² |
| --- | --- | --- | --- |
| Control D | — | — | 39.50 ± 1.85 |
| Example 15 | DL-α-Tocotrienol | 10 | 39.25 ± 1.84 |
| Example 16 | DL-α-Tocotrienol | 30 | 31.75 ± 1.25 |
| Example 17 | DL-α-Tocotrienol | 50 | 0.00 ± 0.00 |
| Example 18 | DL-γ-Tocotrienol | 10 | 4.75 ± 0.48 |
| Example 19 | DL-δ-Tocotrienol | 10 | 0.00 ± 0.00 |
| Example 20 | Tocotrienol Mixture | 10 | 5.50 ± 0.65 |
| Comp. 3 | α-Tocotrienol | 100 | 39.25 ± 2.17 |

From the above results, it can be seen that DL-δ-tocotrienol inhibited lumen formation completely at a concentration of 10 μM, and DL-γ-tocotrienol and tocotrienol mixture also inhibited lumen formation sufficiently. Inhibition of DL-α-tocotrienol against lumen formation was equivalent to the control group at a concentration of 10 μM, but inhibited lumen formation at 30 μM or more, and completely inhibited formation at 50 μM. On the other hand, α-tocopherol did not inhibit lumen formation even at 100 μM.

Examples 21–26
Inhibition against Lumen Formation Induced by FGF

Inhibition by the tocotrienol mixture, DL-α-tocotrienol, DL-β-tocotrienol, DL-γ-tocotrienol and DL-δ-tocotrienol was examined against lumen formation induced by FGF. The test was carried out similar to Examples 12–14, wherein FGF was added together with each tocotrienol. In the case of Control group E, no sample was added.

Comparative Example 4

The test was carried out in the same manner as Example 22, except that α-tocopherol was substituted for DL-α-tocotrienol.

The results are summarized in Table 5, wherein the number of cells forming lumen/cm² are shown by mean value ±SE (n=4).

TABLE 5

| | Sample | Conc. (μM) | Number of Cells Forming Lumen/cm² |
| --- | --- | --- | --- |
| Control E | — | — | 32.25 ± 4.87 |
| Example 21 | FGF 20 ng/ml | — | 35.25 ± 3.77 |
| Example 22 | DL-α-Tocotrienol FGF 20 ng/ml | 10 | 25.25 ± 1.55 |
| Example 23 | DL-β-Tocotrienol FGF 20 ng/ml | 10 | 0.00 ± 0.00 |
| Example 24 | DL-γ-Tocotrienol FGF 20 ng/ml | 10 | 12.50 ± 3.20 |

TABLE 5-continued

| Sample | | Conc. (μM) | Number of Cells Forming Lumen/cm² |
|---|---|---|---|
| Example 25 | DL-δ-Tocotrienol FGF 20 ng/ml | 10 | 0.00 ± 0.00 |
| Example 26 | Tocotrienol Mixture FGF 20 ng/ml | 10 | 5.00 ± 0.58 |
| Comp. 4 | α-Tocopherol FGF 20 ng/ml | 100 | 25.25 ± 2.10 |

From the results of Table 5, it can be seen that DL-α-tocotrienol, DL-β-tocotrienol, DL-γ-tocotrienol and DL-δ-tocotrienol inhibited the lumen formation induced by FGF. Particularly, DL-β-tocotrienol and DL-δ-tocotrienol each inhibited the lumen formation completely at 10 μM.

Examples 27–29

Measurement of LDH Activity

A rate of cell damage of BAEC by the sample was evaluated by measuring free LDH activity in a culture medium using a kit for LDH-cytotoxicity testing (Wako Co.)

BAEC with confluent growth were treated with trypsin, and suspended in MEM | 10% FBS in a concentration of $5 \times 10^4$ cell/ml. The cell suspension was placed in each well of a 96 well-microplate in an amount of 100 μl/well, and incubated overnight in a $CO_2$ incubator. The culture solution in each well was removed, and changed to 100 μl culture medium (MEM+2% FBS) containing a sample to continue incubation. In the experiment, MEM+2% FBS was employed as a negative control (NC), and 2% Tween 20 dissolved in MEM | 2% FBS was employed as a positive control (PC). After 48 hours, 50 μl culture medium in each well was transferred to a new well, and the color producing reagent in the kit was added to the new wells in an amount of 50 μl/well. After incubating for 45 minutes at room temperature, reaction was terminated by adding 100 μl of 0.5 N HCL/well, and absorbance at 595 nm was measured. The rate of cell damage was determined by the following formula:

Rate of Cell Damage=$(S-N)/(P-N) \times 100 (\%)$

S: Absorbance of sample
N: Absorbance of negative control
P: Absorbance of positive control Comparative Examples 5–7

The assay was carried out in the same manner as Examples 27–29, except that the tocotrienol mixture was replaced by α-tocopherol.

The results are summarized in Table 6, wherein the rate of cell damage (% of control) is mean value±SE (n=4).

TABLE 6

| Sample | | Conc. (μM) | Rate of Cell Damage (% of control) |
|---|---|---|---|
| Control F | — | — | 100.00 ± 1.13 |
| Example 27 | Tocotrienol Mixture | 25 | 195.13 ± 1.33 |
| Example 28 | Tocotrienol Mixture | 10 | 122.87 ± 2.03 |
| Example 29 | Tocotrienol Mixture | 1 | 123.97 ± 2.84 |
| Comp. 5 | α-Tocopherol | 100 | 127.01 ± 0.91 |
| Comp. 6 | α-Tocopherol | 25 | 105.11 ± 1.21 |
| Comp. 7 | α-Tocopherol | 10 | 99.39 ± 1.34 |

From the results in Table 6, it can be seen that the cell damage action of tocotrienol is stronger than α-tocopherol.

Examples 30–34

The assay was carried out in the same manner as Examples 27–29, except that the tocotrienol mixture was replaced by DL-α-tocotrienol, DL-β-tocotrienol, DL-γ-tocotrienol and DL-δ-tocotrienol to determine the rate of cell damage (% of control). In Control group G, no sample was added.

Comparative Example 8

The assay was carried out in the same manner as Example 30, except that the tocotrienol was replaced by α-tocopherol.

The results are summarized in Table 7, wherein the rate of cell damage (% of control) is mean value ISE (n=5).

TABLE 7

| Sample | | Conc. (μM) | Rate of Cell Damage (% of control) |
|---|---|---|---|
| Control G | — | | 100.00 ± 1.75 |
| Example 30 | DL-α-Tocotrienol | 10 | 122.67 ± 4.17 |
| Example 31 | DL-β-Tocotrienol | 10 | 211.31 ± 7.05 |
| Example 32 | DL-γ-Tocotrienol | 10 | 265.33 ± 3.18 |
| Example 33 | DL-δ-Tocotrienol | 10 | 252.76 ± 5.46 |
| Example 34 | Tocotrienol Mixture | 10 | 179.36 ± 9.14 |
| Comp. 8 | α-Tocopherol | 100 | 109.61 ± 2.31 |

From the results in Table 7, it can be seen that DL-α-tocotrienol, DL-β-tocotrienol, DL-γ-tocotrienol and DL-δ-tocotrienol have an activity to damage cells. However, the rate of cell damage of α-tocopherol was equivalent to Control group G, even in a concentration of 100 μM, and accordingly, α-tocopherol has no activity to damage cells.

Examples 35–40

Cell damage action of DL-α-tocotrienol, DL-β-tocotrienol, DL-γ-tocotrienol, DL-δ-tocotrienol and the tocotrienol mixture was examined against FGF. The test was carried out according to Examples 27–29, except that FGF was added. In Control group H, no sample was added.

Comparative Example 9

The assay was carried out in the same manner as Example 36, except that the tocotrienol was replaced by α-tocopherol.

The results are summarized in Table 8, wherein the rate of cell damage (% of control) is mean value±SE(n=4).

TABLE 8

| Sample | | Rate of Cell Damage (% of control) |
|---|---|---|
| Control H | — | 100.00 ± 1.75 |
| Example 35 | FGF 20 ng/ml | 102.78 ± 0.79 |
| Example 36 | FGF 20 ng/ml DL-α-Tocotrienol 10 μM | 112.50 ± 4.43 |
| Example 37 | FGF 20 ng/ml DL-β-Tocotrienol 10 μM | 153.50 ± 4.60 |
| Example 38 | FGF 20 ng/ml DL-γ-Tocotrienol 10 μM | 101.15 ± 2.38 |
| Example 39 | FGF 20 ng/ml DL-δ-Tocotrienol 10 μM | 195.79 ± 6.97 |
| Example 40 | FGF 20 ng/ml Tocotrienol Mixture 10 μM | 138.22 ± 3.18 |
| Comp. 9 | FGF 20 ng/ml α-Tocopherol 100 μM | 126.01 ± 1.62 |

Effects of tocotrienol on cell multiplication, lumen formation and cell damage of FGF are summarized in Table 9.

TABLE 9

| | Cell Multiplication | Lumen Formation | Cell Damage |
|---|---|---|---|
| FGF (20 ng/ml) + DL-α-Tocotrienol (10 μM) | ↑ | → | — |
| FGF (20 ng/ml) + DL-β-Tocotrienol (10 μM) | ↓↓ | ↓↓ | + |
| FGF (20 ng/ml) + DL-γ-Tocotrienol (10 μM) | ↑ | ↓ | — |
| FGF (20 ng/ml) + DL-δ-Tocotrienol (10 μM) | ↓↓ | ↓↓ | ++ |
| FGF (20 ng/ml) + Tocotrienol Mixture (10 μM) | ↓ | ↓ | + |
| FGF (20 ng/ml) + α-Tocopherol (100 μM) | ↑ | → | — |
| FGF (20 ng/ml) | ↑ | / | — |

↑: Accelerated
/: Tendency to increase
→: No change
↓: Inhibited
↓↓: Strongly inhibited
—: No toxicity
|: Slightly toxic
++: Toxic As can be seen from Table 9, the tocotrienol mixture, DL-β-tocotrienol, DL-γ-tocotrienol and DL-δ-tocotrienol each exhibit inhibitory action against lumen formation in a concentration of 10 μM (β=δ>α). It is estimated from the aforementioned lumen formation inhibition test that DL-α-tocotrienol exhibits inhibitory action against lumen formation in a concentration of more than 10 μM. One the other hand, inhibitory action of α-tocopherol was not found even at a concentration of 100 μM.

Examples 41–60
Effects of Tocotrienol on Cell Multiplication of BAEC

Influence of tocotrienols on cell multiplication of BAEC was examined in various concentrations. The cell multiplication was evaluated by determining the survival rate of cells using WST-1, which makes it possible to conduct high sensitivity measurement, instead of conventional MTT.

BAEC with confluent growth were treated with trypsin, and suspended in MEM | 10% FBS in a concentration of $2 \times 10^4$ cells/ml. The cell suspension was placed in each well of a 96 well-microplate coated with type I collagen in an amount of 100 μl/well, and incubated 24 hours in a $CO_2$ incubator. As a blank, the culture medium alone was incubated without adding cells. The culture solution in each well was removed, and changed to 100 μl culture medium (MEM+2% FBS) containing a sample to continue incubation. The microplate was taken out after 24 hours from placing the culture medium containing a sample. 10 μl/well of WST-1 solution was added to each well, and incubated in a $CO_2$ incubator. After 3 hours, absorbance at 450 nm and 655 nm (dual) of each well was measured by a microplate reader.

The samples employed were DL-α-tocotrienol, DL-γ-tocotrienol and DL-δ-tocotrienol. In the case of Control group I, no sample was added.

The survival rate of cells was determined by the following formula:

Survival Rate of Cells=$(S-B)/(C-B) \times 100(\%)$

S: Absorbance of sample
C: Absorbance of Control
B: Absorbance of Blank

The results are summarized in Table 10, wherein the survival rate of cells is the mean value±SD(n=9).

TABLE 10

| | Sample | Conc. (μM) | Survival Rate of Cells (% of control) |
|---|---|---|---|
| Control A | — | — | 100.00 ± 6.00 |
| Example 41 | DL-α-Tocotrienol | 25 | 111.0 ± 6.8 |
| Example 42 | DL-α-Tocotrienol | 30 | 115.8 ± 9.2 |
| Example 43 | DL-α-Tocotrienol | 35 | 67.3 ± 11.6 |
| Example 44 | DL-α-Tocotrienol | 40 | 39.1 ± 12.7 |
| Example 45 | DL-α-Tocotrienol | 45 | 6.9 ± 5.9 |
| Example 46 | DL-β-Tocotrienol | 2 | 89.4 ± 5.1 |
| Example 47 | DL-β-Tocotrienol | 4 | 97.8 ± 7.9 |
| Example 48 | DL-β-Tocotrienol | 6 | 57.1 ± 5.9 |
| Example 49 | DL-β-Tocotrienol | 8 | 5.6 ± 5.4 |
| Example 50 | DL-β-Tocotrienol | 10 | 0.0 ± 0.0 |
| Example 51 | DL-γ-Tocotrienol | 10 | 102.3 ± 10.8 |
| Example 52 | DL-γ-Tocotrienol | 12 | 15.5 ± 4.5 |
| Example 53 | DL-γ-Tocotrienol | 14 | 3.4 ± 3.1 |
| Example 54 | DL-γ-Tocotrienol | 16 | 0.0 ± 0.1 |
| Example 55 | DL-γ-Tocotrienol | 18 | 2.0 ± 2.8 |
| Example 56 | DL-δ-Tocotrienol | 2 | 93.0 ± 6.8 |
| Example 57 | DL-δ-Tocotrienol | 4 | 109.4 ± 8.0 |
| Example 58 | DL-δ-Tocotrienol | 6 | 0.9 ± 1.3 |
| Example 59 | DL-δ-Tocotrienol | 8 | 5.8 ± 4.5 |
| Example 60 | DL-δ-Tocotrienol | 10 | 0.4 ± 0.9 |

The tocotrienols exhibited concentration dependent inhibitory action. The strength of the inhibitory action was in the order of DL-α-tocotrienol<DL-γ-tocotrienol<DL-β-tocotrienol<DL-δ-tocotrienol. That is, the cell multiplication inhibitory action of tocotrienols against endothelial cell varies greatly according to the structure of tocotrienols.

The results of Table 10 were made in a graph shown in FIG. 1, and median growth inhibition concentration ($IC_{50}$) was determined from the graph. In the figure, the numbers on the ordinate indicate the survival rate of cells (% of control), and the numbers on the abscissa indicate concentration (μM). ● is DL-α-tocotrienol, ■ is DL-β-tocotrienol, Δ is DL-γ-tocotrienol, and X is DL-δ-tocotrienol, respectively.

The IC$_{50}$ value of each tocotrienol was shown in Table 11.

TABLE 11

| Sample | IC$_{50}$ |
|---|---|
| DL-α-tocotrienol | 38 |
| DL-β-tocotrienol | 6.5 |
| DL-γ-tocotrienol | 11 |
| DL-δ-tocotrienol | 5.5 |

Preparation 1
Tablets

Tablets for oral administration having the following composition were prepared according to a conventional method.

| Tocotrienol mixture | 50 mg |
|---|---|
| Lactose | 50 mg |
| Corn starch | 14 mg |
| Polyvinyl pyrrolidone | 5 mg |
| Mg stearate | 1 mg |

Preparation 2
Tablets

Tablets for oral administration having the following composition were prepared according to a conventional method.

| DL-β-tocotrienol | 50 mg |
|---|---|
| Lactose | 50 mg |
| Corn starch | 14 mg |
| Polyvinyl pyrrolidone | 5 mg |
| Mg stearate | 1 mg |

Preparation 3
Injection for Muscle 100 mg DL-β-tocotrienol was dissolved in 1 ml purified corn oil to prepare an injection for muscle.

Preparation 4
Injection for Muscle 100 mg DL-δ-tocotrienol was dissolved in 1 ml purified corn oil to prepare an injection for muscle.

Preparation 5
Intravenous Injection 50 mg tocotrienol was emulsified in 1 ml pure water with 5 mg polyoxyethylene sorbitan monostearate, and 0.2 mg propylparaben was added to prepare an intravenous injection.

What is claimed is:

1. A method of inhibiting neovasculation in a subject comprising the step of administering a preparation comprising β-tocotrienol and a pharmacologically acceptable carrier to the subject.

2. The method of claim 1, wherein said preparation additionally comprises an antioxidant.

3. The method of claim 1, wherein said preparation additionally comprises at least one member selected from the group consisting of a pH adjustor, a buffer, a resolvent, a suspending agent, an isotonizing agent, a stabilizer and an antiseptic.

4. A method of inhibiting cell multiplication in a subject comprising the step of administering a preparation comprising β-tocotrienol and a pharmacologically acceptable carrier to the subject.

5. The method of claim 4, wherein said preparation additionally comprises an antioxidant.

6. The method of claim 4, wherein said preparation additionally comprises at least one member selected from the group consisting of a pH adjustor, a buffer, a resolvent, a suspending agent, an isotonizing agent, a stabilizer and an antiseptic.

7. A method of inhibiting the formation of lumens in a subject comprising the step of administering a preparation comprising β-tocotrienol and a pharmacologically acceptable carrier to the subject.

8. The method of claim 7, wherein said preparation additionally comprises an antioxidant.

9. The method of claim 7, wherein said preparation additionally comprises at least one member selected from the group consisting of a pH adjustor, a buffer, a resolvent, a suspending agent, an isotonizing agent, a stabilizer and an antiseptic.

10. A method of inhibiting fibroblast growth factor in a subject comprising the step of administering a preparation comprising β-tocotrienol and a pharmacologically acceptable carrier to the subject.

11. The method of claim 10, wherein said preparation additionally comprises an antioxidant.

12. The method of claim 10, wherein said preparation additionally comprises at least one member selected from the group consisting of a pH adjustor, a buffer, a resolvent, a suspending agent, an isotonizing agent, a stabilizer and an antiseptic.

* * * * *